United States Patent [19]
Sahin et al.

[11] Patent Number: 6,140,050
[45] Date of Patent: Oct. 31, 2000

[54] METHODS FOR DETERMINING BREAST CANCER AND MELANOMA BY ASSAYING FOR A PLURALITY OF ANTIGENS ASSOCIATED THEREWITH

[75] Inventors: Ugur Sahin; Özlem Türeci, both of Saar, Germany; Yao-Tseng Chen; Lloyd J. Old, both of New York, N.Y.; Michael Pfreundschuh, Saar, Germany

[73] Assignee: Ludwig Institute for Cancer Research, New York, N.Y.

[21] Appl. No.: 09/105,907

[22] Filed: Jun. 26, 1998

[51] Int. Cl.[7] .............................. C12Q 1/68; C12P 19/34; C07H 21/04
[52] U.S. Cl. .............................. 435/6; 435/91.2; 435/7.2; 435/7.24; 536/23.5; 536/24.31; 536/24.33
[58] Field of Search ................................ 435/6, 7.2, 91.2, 435/7.24; 536/24.31, 24.33, 24.5

[56] References Cited

U.S. PATENT DOCUMENTS

| | | | |
|---|---|---|---|
| 5,342,774 | 8/1994 | Boon et al. | 435/240.2 |
| 5,571,711 | 11/1996 | Van der Bruggen et al. | 435/240.2 |
| 5,610,013 | 3/1997 | Van den Eynde et al. | 435/6 |
| 5,612,201 | 3/1997 | De Plaen et al. | 435/6 |
| 5,648,226 | 7/1997 | Van den Eynde et al. | 435/7.24 |
| 5,698,396 | 12/1997 | Pfreundschuh | 435/6 |
| 5,888,751 | 3/1999 | Tureci et al. | 435/7.23 |

FOREIGN PATENT DOCUMENTS 9716335  9/1997  WIPO.

OTHER PUBLICATIONS

Chen et al. Proceedings of the National Academy of Sciences. 94:1914–1918, Mar. 1997.

Tureci et al., "Identificaion of a Meiosis–Specific Protein as a Member of the Class of Cancer/Testis Antigen" *Proc. Natl. Acad. Sci. USA*, 95:5211–5216 (1998).

Tureci et al., "The SSX–2 Gene, Which is Involved in the t(X;18) Translocation of Synovial Sarcomas, Codes for the Human Tumor Antigen HOM–MEL[1]", *Cancer Research*, 56:4766–4772 (1996).

Tureci et al., "Expression of SSX Genes in Human Tumors", *Int. J. Cancer*, 77:19–23 (1998).

Gure et al., "SSX: A Multigene Family with Several Members Transcribed in Normal Testis and Human Cancer," *Int. J. Cancer*, 72:965–971 (1997).

*Primary Examiner*—Carla J. Myers
*Attorney, Agent, or Firm*—Fulbright & Jaworski, LLP

[57] ABSTRACT

The invention relates to assays for determining breast cancer or melanoma. It has been found that the accuracy of such assays can be improved by assaying samples for three or more known tumor rejection antigen precursors. For breast cancer, the tumor rejection antigen precursors known as SCP-1, NY-ESO-1, and SSX-2 are assayed. For melanoma, SSX-2, NY-ESO-1, and MAGE-3 are assayed. Additional known tumor rejection antigen precursors can also be determined to confirm the assays. It is preferred to carry these out via polymerase chain reactions.

15 Claims, No Drawings

METHODS FOR DETERMINING BREAST CANCER AND MELANOMA BY ASSAYING FOR A PLURALITY OF ANTIGENS ASSOCIATED THEREWITH

FIELD OF THE INVENTION

This invention relates to the determination of cancer, melanoma and breast cancer in particular. The methods involve assaying for members of the so-called "cancer-testis" or "CT" antigen family.

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets," i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of such materials, of course, presupposes a source of the reagents used to generate these. Purification from cells is one laborious, far from sure method of doing so. Another preferred method is the isolation of nucleic acid molecules which encode a particular marker, followed by the use of the isolated encoding molecule to express the desired molecule.

To date, two strategies have been employed for the detection of such antigens in, e.g., human tumors. These will be referred to as the genetic approach and the biochemical approach. The genetic approach is exemplified by, e.g., dePlaen et al., Proc. Natl. Sci. USA, 85:2275 (1988), incorporated by reference. In this approach, several hundred pools of plasmids of a cDNA library obtained from a tumor are transfected into recipient cells, such as COS cells, or into antigen-negative variants of tumor cell lines. Transfectants are screened for the expression of tumor antigens via their ability to provoke reactions by anti-tumor cytolytic T cell clones. The biochemical approach, exemplified by, e.g., Mandelboim et al., Nature, 369:69 (1994) incorporated by reference, is based on acidic elution of peptides which have bound to MHC-class I molecules of tumor cells, followed by reversed-phase high performance liquid chromography (HPLC). Antigenic peptides are identified after they bind to empty MHC-class I molecules of mutant cell lines, defective in antigen processing, and induce specific reactions with cytotoxic T-lymphocytes. These reactions include induction of CTL proliferation, TNF release, and lysis of target cells, measurable in an MTT assay, or a $^{51}$Cr release assay.

These two approaches to the molecular definition of antigens have the following disadvantages: first, they are enormously cumbersome, time-consuming and expensive; second, they depend on the establishment of cytotoxic T cell lines (CTLs) with predefined specificity; and third, their relevance in vivo for the course of the pathology of disease in question has not been proven, as the respective CTLs can be obtained not only from patients with the respective disease, but also from healthy individuals, depending on their T cell repertoire.

The problems inherent to the two known approaches for the identification and molecular definition of antigens is best demonstrated by the fact that both methods have, so far, succeeded in defining only very few new antigens in human tumors. See, e.g., van der Bruggen et al., Science, 254:1643–1647 (1991); Brichard et al., J. Exp. Med., 178:489–495 (1993); Coulie et al., J. Exp. Med., 180:35–42 (1994); Kawakami et al., Proc. Natl. Acad. Sci. USA, 91:3515–3519 (1994).

Further, the methodologies described rely on the availability of established, permanent cell lines of the cancer type under consideration. It is very difficult to establish cell lines from certain cancer types, as is shown by, e.g., Oettgen et al., Immunol. Allerg. Clin. North. Am., 10:607–637 (1990). It is also known that some epithelial cell type cancers are poorly susceptible to CTLs in vitro, precluding routine analysis. These problems have stimulated the art to develop additional methodologies for identifying cancer associated antigens.

One key methodology is described by Sahin et al., Proc. Natl. Acad. Sci. USA, 92:11810–11913 (1995), incorporated by reference. Also, see U.S. patent application Ser. No. 08/580,980, filed on Jan. 3, 1996 and U.S. Pat. No. 5,698, 396. All three of these references are incorporated by reference. To summarize, the method involves the expression of cDNA libraries in a prokaryotic host. (The libraries are secured from a tumor sample). The expressed libraries are then immunoscreened with absorbed and diluted sera, in order to detect those antigens which elicit high titer humoral responses. This methodology is known as the SEREX method ("Serological identification of antigens by Recombinant Expression Cloning"). The methodology has been employed to confirm expression of previously identified tumor associated antigens, as well as to detect new ones. See the above referenced patent applications and Sahin et al., supra, as well as Crew et al., EMBO J., 144:2333–2340 (1995).

The SEREX methodology has been applied to esophageal cancer samples, and an esophageal cancer associated antigen has now been identified, and its encoding nucleic acid molecule isolated and clones, as per U.S. patent application Ser. No. 08/725,182 filed Oct. 3, 1996, incorporated by reference herein.

The relationship between some of the tumor associated genes and a triad of genes, known as the SSX genes, was investigated by Sahin et al., supra, and Tureci et al., Cancer Res., 56:4766–4772 (1996). For example, one of these SSX genes, referred to as SSX-2, was identified, at first, as one of two genes involved in a chromosomal translocation event (t(X; 18) (p11.2; q 11.2)), which is present in 70% of synovial sarcomas. See Clark et al., Nature Genetics, 7:502–508 (1994); Crew et al., EMBO J., 14:2333–2340 (1995). It was later found to be expressed in a number of tumor cells, and is now considered to be a tumor associated antigen referred to as HOM-MEL-40 by Tureci et al., supra. Its expression to date has been observed in cancer cells and normal testis only. Thus, parallels other members of the "CT" family of tumor antigens, since they are expressed only in cancer and testis cells. Crew et al. also isolated and cloned the SSX-1 gene, which has 89% nucleotide sequence homology with SSX-2. See Crew et al., supra. Additional work directed to the identification of SSX genes has resulted in the identification of SSX-3, as is described by DeLeeuw et al., Cytogenet. Genet., 73:179–183 (1996). The fact that SSX presentation parallels other, CT antigens suggested to the inventors that other SSX genes might be isolated. See Gure et al., Int. J. Cancer, 72:965–971 (1997), incorporated by reference.

Application of a modification of the SEREX technology described, supra, has been used, together with other techniques, to clone two, additional SSX genes, referred to as SSX4 and SSX5 hereafter, as well as, an alternate splice variant of the SSX4 gene. Specifically, while the SEREX methodology utilizes autologous serum, the methods set forth infra, use allogenic serum. See U.S. patent application Ser. No. 08/851,138, filed May 5, 1997, incorporated by reference.

These investigations have all led to the identification of antigens associated with cancer and, in many cases, the isolation of previously unknown molecules. Exemplary of these are MAGE-1, which is disclosed in, e.g., U.S. Pat. No. 5,342,774 and van der Bruggen et al., *Science*, 254:1643–1647 (1991), incorporated by reference. These references also disclose MAGE-3, which is also described in allowed U.S. patent application Ser. No. 08/037,230, filed Mar. 26, 1993, incorporated by reference.

With respect to the members of the SSX family discussed herein, SSX-1 is disclosed by Crew et al., *EMBO J.*, 14:2333–2340 (1995), incorporated by reference. The SSX-2 gene is disclosed by Clark et al., *Nature Genetics*, 7:502–508 (1994). Independently, Pfreundschuh identified the so-called "HOM-MEL 40" gene as a cancer associated antigen, as is described in U.S. Pat. No. 5,698,396, also incorporated by reference. The SSX4 gene is described in Ser. No. 08/851,138, filed Mar. 5, 1997 and incorporated by reference. Also see Gure et al., *Int. J. Cancer*, 72:965–971 (1997), incorporated by reference. With respect to SCP-1, see U.S. patent application Ser. No. 08/892,702 filed Jul. 15, 1997, and incorporated by reference, and Meuwissen et al., *EMBO J.*, 11(13):5091–5100 (1992), also incorporated by reference. For NY-ESO-1, see allowed U.S. patent application Ser. No. 08/725,182, filed Oct. 3, 1996, and Chen et al., *Proc. Natl. Acad. Sci. USA*, 94:1914–1918 (1997), incorporated by reference. BAGE, another of the antigens in this family, is described in U.S. Pat. No. 5,571,711, and Boel et al., *Immunity*, 2:167–175 (1995), incorporated by reference. The GAGE antigen is described, e.g., in U.S. Pat. Nos. 5,610,013 and 5,648,226, both of which are incorporated by reference. Several members of the GAGE family are described in these references; however, due to their high degree of homology, GAGE is used in the singular hereafter to refer to this family of related molecules because in the experiments which follow, the primers used will identify all forms of the gene.

Expression of these antigens is associated with cancer; however, there is no antigen, including the specific antigens discussed herein, which have been found to be expressed in all tumors. Further, there has not been any tumor type observed, wherein expression of the antigen is ubiquitous. Hence, further efforts are needed to correlate expression of these antigens with tumor types.

It has now been found that by carrying out multiple assays, one can develop a clearer idea of whether or not breast cancer or melanoma is present in a patient sample. This diagnostic approach is one feature of the invention. This, in turn, has therapeutic implications, because one can develop therapeutic approaches such as peptide cocktails, based upon the pattern of expression found in a particular tumor sample. This can include, e.g., the mixing of tumor rejection antigens, which are peptides derived from the longer antigens and are known to associate with MHC molecules, provoking cytolytic T cell line proliferation use of such peptides requires HLA typing of the subject under consideration, but this is a standard technique well-known to the art. Further, one can compare the expressed antigens to determine regions of homology within tumor rejection antigen sequences, so as to determine the smallest number of so-called "TRAs" necessary to provoke a response.

These, and other aspects of the invention, will become clear from the disclosure which follows:

DETAILED DESCRIPTION OF PREFERRED EMBODIMENTS

EXAMPLE 1

A set of experiments were carried out to determine which of the CT antigens were expressed in breast cancer and melanoma. A total of 51 specimens of primary breast carcinomas, and 23 malignant melanomas were screened, via reverse transcription PCR, (i.e., "RT-PCR"). In each case, amplification was carried out using 0.25 U Taq polymerase, in a 25 µl reaction volume. The annealing temperature was 60° C., and 35 cycles were carried out. The primers used were the following.

```
For SSX1:              5'-CTAAAGCATC AGAGAAGAGA AGC-3'
                       5'-AGATCTCTTA TTAATCTTCT CAGAAA-3'
(SEQ ID NOS:1 and 2)

For SSX2:              5'-AAAATCAGAG TCAGACTGCT CCCGGTC-3'
                       5'-GTACATGCTG ACCAGGAAAC AGAGTGA-3'
(SEQ ID NOS:3 and 4)

For SSX4:              5'-AAATCGTCTA TGTGTATATG AAGCT-3'
                       5'-GGGTCGCTGA TCTCTTCATA AAC-3'
(SEQ ID NOS:5 and 6)

For SCP-1:             5'-GTACAGCAGA AAGCAAGCA ACTGAATG
                       5'-GAAGGAACTG CTTTAGAATC CAATTTCC-3'
(SEQ ID NOS:7 and 8)

For NY-ESO-1:          5'-CACACAGGAT CCATGGATGC TGCAGATGCG G-3'
                       5'-CACACAAAGC TTGGCTTAGC GCCTCTGCCC TG
(SEQ ID NOS:9 and 10)

For MAGE-1:            5'-CGGCCGAAGG AACCTGACCC AG-3'
                       5'-GCTGGAACCC TCACTAGGTT GCC-3'
(SEQ ID NOS:11 and 12)

For MAGE-3:            5'-GGCCCAGGCT CGGTGAGGAG G-3'
                       5'-GGACGATTAT CAGGAGGGCC TGC-3'
(SEQ ID NOS:13 and 14)
```

-continued

```
For GAGE:            5'-GCGGCCCGAG CAGTTCA-3'
                     5'-CCATCAGGAC CATCTTCA-3'
(SEQ ID NOS:15 and 16)

and for BAGE:        5'-GCTGGAGCCT GTAACACCGT GGC-3'
                     5'-GTATATAGAA ATACTGCACA GTCC-3'
(SEQ ID NOS:17 and 18)
```

See Gure et al., *Int. J. Cancer*, 72:965–971 (1997), Tureci et al., *Canc. Res.*, 56:4766–4772 (1996) and U.S. patent application Ser. No. 08/185,138, filed on May 5, 1997, incorporated by reference, for information on SSX assays. For SCP-1, see Tureci et al., *Proc. Natl. Acad. Sci. USA*, 95:5215–5216 (1998) and U.S. patent application Ser. No. 08/851,137, filed May 5, 1997, incorporated by reference. For NY-ESO-1, see allowed U.S. patent application Ser. No. 08/725,182, filed Oct. 3, 1996, incorporated by reference, and Chen et al., *Proc. Natl. Acad. Sci. USA*, 94:1914–1918 (1997), incorporated by reference. For MAGE-1, see U.S. Pat. No. 5,342,774, incorporated by reference, van der Bruggen et al., *Science*, 254:1643–1647 (1991), and Weynants et al., *Int. J. Cancer*, 56:826–829 (1994), both of which are incorporated by reference. For GAGE, see U.S. Pat. Nos. 5,610,013 and 5,648,226 and van den Eynde et al., *J. Exp. Med.*, 182:689–698 (1995), incorporated by reference. The primers for BAGE and MAGE-3 provided, supra, (i.e., SEQ ID NOS: 13, 14, 17, and 18) are newly designed. Of the samples tested, 27 breast cancer samples were positive, and 17 melanoma samples were positive.

The details of the PCR work are as follows. For SSX-1, the assay consisted of 10 minutes at 94° C., followed by 35 cycles of 1 minute at 56° C. for annealing, followed by 2 minutes at 72° C., 1 minute at 94° C., and one final extension of 8 minutes at 72° C. This final extension was the same for each PCR protocol. For SSX-2, the first 10 minutes were at 95° C. A cycle was 1 minute at 67° C. for annealing, two minutes at 72° C., and one minute at 94° C. For SSX-4, the protocol was the same as SSX-2, except the annealing step was 1 minute at 60° C. For ESO-1, annealing required 1 minute at 65° C., and the cycle was identical to the SSX-2 cycle otherwise. The first heating step required 2 minutes at 94° C. The SCP-1 protocol required 2 minutes at 94° C., followed by 35 cycles identical to SSX-2, except annealing required 1 minute at 60° C. The MAGE-3 cycle was identical to MAGE-1, except annealing required 1 minute at 63° C. Similarly, the GAGE protocol required 1 minute at 52° C. for annealing, while the BAGE cycle required 1 minute at 58° C. for annealing. The results are set forth in the two Tables which follow. Table 1 presents data from breast cancer, while Table 2 presents work from melanoma.

TABLE 1

| Total 27/51(53%) | SSX1 | SSX2 | SSX4 | SCP1 | NY-EsoI | MAGE1 | MAGE3 | GAGE | BAGE |
|---|---|---|---|---|---|---|---|---|---|
| Ma 1  | -    | +    | -    | -    | -    | -    | -    | -    | -    |
| Ma 2  | -    | -    | -    | -    | -    | -    | -    | -    | +    |
| Ma 3  | -    | -    | -    | +    | +    | +    | -    | -    | -    |
| Ma 4  | -    | -    | -    | +    | -    | -    | -    | -    | -    |
| Ma 5  | -    | +    | -    | -    | -    | -    | -    | -    | -    |
| Ma 6  | -    | -    | -    | -    | -    | +    | +    | +    | -    |
| Ma 7  | -    | -    | -    | +    | +    | -    | -    | -    | -    |
| Ma 8  | +    | +    | +    | +    | +    | -    | +    | +    | -    |
| Ma 9  | -    | -    | -    | -    | -    | -    | +    | -    | -    |
| Ma 10 | +    | -    | -    | -    | +    | +    | +    | -    | -    |
| Ma 11 | +    | -    | -    | +    | +    | -    | -    | -    | -    |
| Ma 12 | -    | -    | +    | +    | +    | -    | -    | -    | -    |
| Ma 13 | -    | -    | +    | -    | -    | -    | +    | -    | -    |
| Ma 14 | -    | +    | -    | -    | -    | -    | +    | +    | -    |
| Ma 15 | -    | -    | -    | +    | +    | -    | -    | -    | -    |
| Ma 16 | -    | -    | -    | -    | -    | -    | -    | +    | -    |
| Ma 17 | -    | -    | -    | +    | +    | -    | -    | -    | -    |
| Ma 18 | -    | -    | -    | -    | +    | -    | -    | -    | -    |
| Ma 19 | -    | -    | -    | -    | -    | +    | -    | -    | -    |
| Ma 20 | -    | -    | -    | +    | -    | -    | -    | -    | -    |
| Ma 21 | -    | -    | +    | +    | -    | -    | -    | -    | -    |
| Ma 22 | -    | -    | +    | +    | +    | -    | -    | -    | -    |
| Ma 23 | +    | -    | +    | +    | -    | -    | +    | -    | -    |
| Ma 24 | -    | -    | -    | +    | -    | -    | -    | -    | -    |
| Ma 25 | -    | -    | -    | +    | -    | -    | -    | -    | -    |
| Ma 26 | +    | -    | +    | +    | -    | -    | -    | -    | -    |
| Ma 27 | -    | -    | -    | +    | +    | -    | -    | -    | -    |
| number (%) | 6 (12) | 4 (8) | 7 (14) | 16 (31) | 12 (24) | 4 (8) | 7 (14) | 4 (8) | 1 (2) |

TABLE 2

| 17/23 (74%) | SSX1 | SSX2 | SSX4 | SCP1 | NY-EsoI | MAGE1 | MAGE3 | GAGE | BAGE |
|---|---|---|---|---|---|---|---|---|---|
| Mm 1 | + | + | + | + | + | + | + | + | + |
| Mm 2 | - | - | - | - | + | + | + | - | + |
| Mm 3 | - | - | - | - | + | - | - | - | - |
| Mm 4 | - | - | - | - | - | - | + | - | - |
| Mm 5 | - | - | - | - | + | - | + | + | - |
| Mm 6 | - | + | - | - | + | + | + | - | + |
| Mm 7 | - | + | - | - | - | - | - | - | - |
| Mm 8 | - | + | + | + | + | + | + | - | - |
| Mm 9 | - | - | - | - | - | - | - | - | + |
| Mm 10 | + | + | + | - | - | + | + | - | + |
| Mm 11 | + | + | - | - | - | - | - | + | - |
| Mm 12 | + | + | + | - | - | + | + | - | - |
| Mm 13 | + | + | + | - | - | - | - | - | - |
| Mm 14 | + | - | - | - | - | + | + | - | - |
| Mm 15 | - | + | + | - | + | - | + | + | - |
| Mm 16 | + | + | - | - | + | + | + | - | - |
| Mm 17 | - | - | - | - | + | - | + | - | - |
| number (%) | 7 (30) | 10 (44) | 6 (26) | 2 (8) | 10 (44) | 8 (35) | 12 (52) | 4 (17) | 5 (22) |

It was found that SCP-1 showed the highest expression rate in breast cancer (31%), while NY-ESO-1 also showed high expression (24%).

With respect to melanoma, MAGE-3 showed the highest incidence of expression (53%), followed by NY-ESO-1 (44%), and SSX-2 (44%). Only 9% of the samples tested were positive for SCP-1.

It is of interest that, of the 27 breast cancer samples which were positive for at least one of the molecules tested, all but 5 were positive for one or more of SSX-2, SCP-1, and NY-ESO-1 of the 5 samples which tested negative for the three primary expression products, four of these could be determined if at least one of MAGE-1, MAGE-3, and GAGE were added to the screen, because each of these molecules was expressed in two of the five samples negative for SSX-2, MAGE-1, and SCP-1.

With respect to the melanoma assays, previous work had determined that each of the molecules tested was present in at least some melanoma samples; however, it has also been shown that not all melanomas express the same patterns of tumor rejection antigens. For example, as indicated supra, MAGE-3, NY-ESO-1, and SSX-2 have the highest ratios of expression, but it is not 100% for any of these. In situations which screening for one of these three clones was negative, confirming assays were positive in all but one case. Hence, one can verify presence of melanoma by screening for all three of the preferred antigens, i.e., SSX-2, NY-ESO-1, and MAGE-3.

EXAMPLE 2

The amino acid sequence of the genes referred to herein were in part analyzed, for peptide sequences which correspondence to HLA binding motifs. This was done using the algorithm taught by Parker et al., J. Immunol. 142: 163 (1994), incorporated by reference. In the Table which follows, the amino acid sequence, the HLA molecule to which it presumably binds, and the positions in SCP-1 are given. The resulting complexes should provoke a cytolytic T cell response. This could be determined by one skilled in the art following methods taught by, e.g., van der Bruggen, et al., J. Eur. J. Immunol. 24: 3038–3043 (1994), incorporated by reference.

| MHC MOLECULE | PEPTIDE | POSITION |
|---|---|---|
| For SCP-1 | | |
| A1 | NSEGLSRVY | 98–106 |
| A1 | SSELEEMTK | 416–424 |
| A1 | EVELEELKK | 430–438 |
| A1 | CTEDDFEFPF | 41–50 |
| A1 | NIDSDPALQK | 61–70 |
| A1 | RTEQQRLENY | 392–401 |
| A1 | IADEAVKLQK | 685–694 |
| A1 | IAEMVALMEK | 704–713 |
| A2 | KLYKEAEKI | 108–116 |
| A2 | KLQENRKII | 133–141 |
| A2 | KMITAFEEL | 220–228 |
| A2 | VVTEFETTV | 376–384 |
| A2 | VELEELKKV | 431–439 |
| A2 | VLGEKETLL | 439–447 |
| A2 | LLQAREKEV | 470–478 |
| A2 | RMLTQIENL | 554–562 |
| A2 | NLQETETQL | 561–569 |
| A2 | QLNVYEIKV | 632–640 |
| A2 | NLLEEVEKA | 674–682 |
| A2 | KMREDRWAV | 947–955 |
| A2 | ALQKVNFLPV | 67–76 |
| A2 | FLLEESRDKV | 287–296 |
| A2 | KLTHJKEVEL | 424–433 |
| A2 | KQFEKIAEEL | 451–460 |
| A2 | GLLQAREKEV | 469–478 |
| A2 | TQLRNELEYV | 567–576 |
| A2 | KQVENKNKYI | 603–612 |
| A2 | KQLNVYEIKV | 631–640 |
| A2 | NVYEIKVNKL | 634–643 |
| A2 | YLWTSAKNTL | 835–844 |
| A2 | KLKEAEKLFV | 964–973 |
| A3 | KLSSKRELK | 502–510 |
| A3 | NLRKQVENK | 600–608 |
| A3 | TLGGDSTFFK | 27–36 |
| A3 | KLYKEAEKIK | 108–117 |
| A3 | KMITAFEELR | 220–229 |
| A3 | LLYDNKQFEK | 446–455 |
| A3 | KLELELESAK | 642–651 |
| A3 | LLETPDIYWK | 797–806 |
| A24 | VYMDLNSNI | 210–218 |

-continued

| MHC MOLECULE | PEPTIDE | POSITION |
|---|---|---|
| A24 | NYEDQLIIL | 400–408 |
| A24 | VYEIKVNKL | 635–643 |
| A24 | LYDNKQFEKI | 447–456 |
| B7 | AQRKAIQEL | 143–151 |
| B7 | ATRHLCNLL | 178–186 |
| B7 | TPKKAPSSL | 925–933 |
| B7 | DPALQKVNFL | 65–74 |
| B7 | QAREKEVHDL | 472–481 |
| B7 | LPKRGQRPKL | 494–503 |
| B7 | RPKLSSKREL | 500–509 |
| B7 | KPKLQQRENL | 859–868 |
| B8 | ELRQKESKL | 126–143 |
| B8 | ESRDKVNQL | 291–299 |
| B8 | SAKQKFGEI | 649–657 |
| B8 | ISKDKRDYL | 828–836 |
| B8 | IAKMDRKKKL | 956–965 |
| B35 | ISKDKRDY (8MER) | 828–835 |
| B35 | TPKKAPSSL | 925–933 |
| B35 | LPKRGQRPKL | 494–503 |
| B35 | RPKLSSKREL | 500–509 |
| B35 | KSKEQEQSSL | 733–742 |
| B35 | KPKLQQRENL | 859–868 |
| B44 | TEDDFEFPF | 42–50 |
| B44 | KEAEKIKKW | 111–119 |
| B44 | AEKTKKYEY | 194–202 |
| B44 | TEQQRLENY | 393–401 |
| B44 | RELKNTEYF | 507–515 |
| B44 | AESKQLNVY | 628–636 |
| B44 | EEETLKTLY | 903–911 |
| B44 | YEREETRQVY | 202–211 |
| B44 | AENSRLEMHF | 232–241 |
| B44 | KENKMKDLTF | 278–287 |
| B44 | REKEVHDLEY | 474–483 |
| B44 | KEVHDLEYSY | 476–485 |
| B44 | DEVKCKLDKS | 585–594 |
| B44 | LELESAKQKF | 645–654 |
| B44 | EERKSELGLY | 723–732 |
| B44 | SEEETLKTLY | 902–911 |
| B52 | KQKPFALFV | 3–11 |
| B52 | LQIATNTIC | 345–353 |
| B52 | ENYEDQLII | 399–407 |
| B52 | CQHKIAEMV | 700–708 |
| B52 | LQKVNFLPVL | 68–77 |
| SSX-2 | | |
| A2 | KIQKAFDDI | 20–28 |
|  | KASEKIFYV | 41–49 |
|  | AMTKLGFKA | 57–65 |
|  | RLQGISPKI | 103–111 |
|  | RLRERKQLV | 167–175 |
| A3 | TLPPFMCNK | 66–74 |
|  | KIFYVYMKRK | 45–54 |
| A24 | KYEAMTKLGF | 54–63 |
| B7 | RPQMTFGRL | 96–104 |
|  | GPQNDGKEL | 131–139 |
| B8 | RLRERKQL | 167–174 |
| B35 | FSKEEWEKM | 32–40 |
| B44 | YEAMTKLGF | 55–63 |
|  | RERKQLVIY | 169–177 |
| B52 | LQGISPKIM | 104–112 |
|  | KQLVIYEEI | 172–180 |
| SSX-1 | | |
| A2 | AMTKLGEKV | 57–65 |
|  | AMTKLGFKV | 56–65 |
| A3 | TLPPFMCNK | 66–74 |
| A24 | NYKAMTKLGF | 54–63 |
| B7 | HPQMTFGRL | 96–104 |
|  | GPQNDGKOL | 131–139 |
| B8 | RLRERKQL | 167–174 |
| B44 | RERKQLVIY | 169–177 |
| B52 | KQLVIYEEI | 172–180 |
|  | MTFGRLHRII | 99–108 |

A comparable listing for ESO-1 can be found in U.S. patent application Ser. No. 09/062,422, filed Apr. 17, 1998 and incorporated by reference, at example 6. MAGE derived peptides, including peptides from MAGE-1 and MAGE-3, may be found in U.S. Pat. No. 5,405,940, incoporated by reference. Peptides derived from GAGE may be found in, e.g., Ser. No. 08/602,039, filed Feb. 15, 1996, and incorporated by reference. Peptides from SSX-2, also referred to as Mel-40, can be found, e.g., in Ser. No. 08/644,116, filed May 10, 1996 incorporated by reference. One could easily carryout the same type of analysis using the Parker algorithim for SSX-1 or any other of the genes referred to herein.

One aspect of the invention is a method for determining presence of breast cancer in a sample, which comprises assaying of SSX-2, SCP-1, and NY-ESO-1. All three assays should be carried out, because a negative result in one of these assays does not necessarily mean that breast cancer is not present, as Table 1 shows; however, the Table also shows that by carrying out the confirmance assays, presence of breast cancer is generally confirmed.

Similarly, assays for melanoma can be carried out, by assaying for all of SSX-2, NY-ESO-1, and MAGE-3. The same type of confirmance pattern is seen when this is carried out. For breast cancer, one can then carry out a second assay, to determine if any of MAGE-1, MAGE-3, or GAGE, or some combination of these is present.

As indicated, supra, the oligonucleotide primers represented by SEQ ID NOS: 13, 14, 17 and 18 are new and are a further aspect of the invention, especially since they can be used, e.g., in assays to determine cancers other than breast cancer or melanoma.

The genes referred to herein are expressed in cells of the tumor type listed, thereby enabling the skilled artisan to utilize these for, e.g., assaying for cancer. The determination of expression can be carried out via, e.g., determination of transcripts of a gene or genes, via nucleic acid hybridization, such as via polymerase chain reaction. In a preferred embodiment, on determines presence of a transcript of the genes by contacting a sample with a nucleic acid molecule which specifically hybridizes to the transcripts, such as the specific primers listed.

The hybridization of the nucleic acid molecule to a target is indicative of expression of an gene of interest and of the possibility of cancer. Preferably, this is done with two primer molecules, as in a polymerase chain reaction. Determination of expression of more than one gene in the context of these assays is a part of the invention. The sequences of the targeted genes, as indicated, may be found in the references incorporated herein.

Alternate assays are also a part of the invention. Members of the CT family, such as SSX-2, SCP-1, and NY-ESO-1, are known to provoke antibodies in the individual who expresses a CT family member. Hence, one can carry out the assays described herein via, e.g., determining antibodies in a sample taken from a subject in question. Most preferably, the sample being analyzed is serum. Such assays can be carried out in any of the standard ways one determines antibodies, such as by contacting the sample with an amount of protein or proteins, and any additional reagents necessary to determine whether or not the antibody binds. One approach involves the use of immobilized protein, where the protein is immobilized in any of the standard ways known to the art, followed by contact with the sample and then, e.g., anti-IgG, anti-Fc antibodies, and so forth. Conversely, presence of a CT protein can also be determined, using antibodies in the place of the proteins of the above described assays. Such assays can be combined with nucleic acid based assays, if desired.

The correlation of gene expression with cancer also suggests various therapeutic methods and compositions useful in treating conditions associated with abnormal gene expression. "Abnormal gene expression" in this context may mean expression per se, or levels which differ from those in a normal individual, i.e., they may be lower or higher, with reference to the genes of interest.

The invention envisions therapeutic approaches such as the use of antisense molecules to inhibit or block expression. This antisense molecules are oligonucleotides which hybridize to the nucleic acid molecules and inhibit their expression. Preferably, these are 17–50 nucleotides in length. These antisense oligonucleotides are preferably administered in combination with a suitable carrier, such as a cationic liposome.

Other therapeutic approaches include the administration of proteins per se, one or more antigenic peptides derived therefrom, as well as so-called polytopic vaccines. These include a plurality of antigenic peptides, untied together, preferably by linker sequences, which bind to either MHC-I or MHC-II molecules. These proteins, peptides, or polytopic vaccines may be administered in combination with an appropriate adjuvant. They may also be administered in the form of genetic constructs which are designed to permit expression of the protein, the peptide, the polytopic structures, etc. Peptides and polytopic structures can be expressed by so-called "minigenes" i.e., DNA molecules designed to express portions of the entire molecule, or the various portions of the molecules, linked together as described supra. One can formulate the therapeutic compositions and approaches described herein such that one, or more than one protein, is used as the source of the compositions. In other words, if a whole protein approach is used, one molecule may be used, or two or more may be combined in one formulation. For peptides, these can all be taken from one molecule, or be combinations of peptides taken from more than one. The polytopic structures described herein can also be made up of components of one or more than one molecule.

The amount of agent administered and the manner in which it is administered will, vary, based on the condition being treated and the individual. Standard forms of administration, such as intravenous, intradermal, subcutaneous, oral, rectal and transdermal administration can be used. With respect to formulations, the proteins and/or peptides may be combined with costimulatory molecules, or adjuvants and/or carriers such as a saponin, GM-CSF, one of more interleukin, emulsifying oils such as vitamin E, one or more heat shock protein, etc.

When the nucleic acid approach is utilized, various vectors, such as Vaccinia or adenovirus based vectors can be used. Any vector useful in eukaryotic transfection, such as in transfection of human cells, can be used. These vectors can be used to produce, e.g., cells such as dendritic cells which present relevant peptide/MHC complexes on their surface. The cells can then be rendered non-proliferative prior to their administration, using standard methodologies.

Other aspects of the invention will be clear to the skilled artisan and need not be repeated herein.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A method for determining breast cancer cells in a sample comprising assaying said sample for expression of SCP-1, NY-ESO-1 and SSX-2, by assaying for mRNA or cDNA for SCP-1, NY-ESO-1 or SSX-2, wherein expression of at least one of SCP-1, NY-ESO-1 AND SSX-2 is indicative of the presence of breast cancer cells in said sample.

2. The method of claim 1, wherein expression of two of SCP-1, NY-ESO-1 and SSX-2 is indicative of possible breast cancer in said sample.

3. The method of claim 2, wherein said two of SCP-1, NY-ESO-1, and SSX-2 are SCP-1 and NY-ESO-1.

4. The method of claim 1, further comprising assaying said sample for at least one of MAGE-1, GAGE, and MAGE-3.

5. The method of claim 1, further comprising assaying said sample for at least one SSX-1 and SSX-4.

6. The method of claim 1, wherein said assaying comprises performing a nucleic acid hybridization assay.

7. The method of claim 6, wherein said nucleic acid hybridization assay is a polymerase chain reaction.

8. The method of claim 7 wherein said polymerase chain reaction is carried out with the oligonucleotides consisting of SEQ ID NOS: 3 and 4, SEQ ID NOS: 7 and 8, or SEQ ID NOS: 9 and 10.

9. A method for determining presence of melanoma cells in a sample, comprising assaying said sample for expression of SSX-2, NY-ESO-1 AND MAGE-3 by assaying for mRNA or cDNA for SSX-2, NY-ESO-1 or MAGE-3, wherein expression of at least two of SSX-2, NY-ESO-1 and MAGE-3 is indicative of melanoma cells in said sample.

10. The method of claim 9, wherein said at least two are NY-ESO-1 and MAGE-3.

11. The method of claim 9, wherein said at least two are SSX-2 and MAGE-3.

12. The method of claim 9, wherein expression of all of SSX-2, NY-ESO-1 and MAGE-3 is indicative of possibility of melanoma in said sample.

13. The method of claim 9, comprising determining expression via a nucleic acid hybridization assay.

14. The method of claim 13, wherein said nucleic acid hybridization assay is a polymerase chain reaction.

15. The method of claim 14, wherein said polymerase chain reaction is carried out with the oligonucleotides whose nucleotide sequences are set forth at SEQ ID NOS: 3 and 4, SEQ ID NOS: 9 and 10, or SEQ ID NOS: 13 and 14.

* * * * *

UNITED STATES PATENT AND TRADEMARK OFFICE
CERTIFICATE OF CORRECTION

PATENT NO. : 6,140,050
DATED : October 31, 2000
INVENTOR(S) : Sahin et al

Page 1 of 1

It is certified that error appears in the above-identified patent and that said Letters Patent is hereby corrected as shown below:

In column 6, Table 1, column 1, row entitled Ma 21, change "-" to -- + --.

Signed and Sealed this

Tenth Day of July, 2001

Attest:

*Attesting Officer*

NICHOLAS P. GODICI
*Acting Director of the United States Patent and Trademark Office*

SEQUENCE LISTING

```
<160> NUMBER OF SEQ ID NOS: 18

<210> SEQ ID NO 1
<211> LENGTH: 23
<212> TYPE: DNA
<213> ORGANISM: Homo sapiens
<220> FEATURE:

<400> SEQUENCE: 1 ctaaagcat c      agagaagaga     agc                             23

<210> SEQ ID NO 2
<211> LENGTH: 26
<212> TYPE: DNA
<213> ORGANISM: Homo sapiens
<220> FEATURE:

<400> SEQUENCE: 2
agatctctta     ttaatcttct     cagaaa                            26

<210> SEQ ID NO 3
<211> LENGTH: 27
<212> TYPE: DNA
<213> ORGANISM: Homo sapiens
<220> FEATURE:

<400> SEQUENCE: 3
aaaatcagag     tcagactgct     cccggtc                           27
```

```
<210> SEQ ID NO 4
<211> LENGTH: 27
<212> TYPE: DNA
<213> ORGANISM: Homo sapiens
<220> FEATURE:

<400> SEQUENCE: 4
gtacatgctg    accaggaaac    agagtga                                27

<210> SEQ ID NO 5
<211> LENGTH: 25
<212> TYPE: DNA
<213> ORGANISM: Homo sapiens
<220> FEATURE:

<400> SEQUENCE: 5
aaatcgtcta    tgtgtatatg    aagct                                  25

<210> SEQ ID NO 6
<211> LENGTH: 23
<212> TYPE: DNA
<213> ORGANISM: Homo sapiens
<220> FEATURE:

<400> SEQUENCE: 6
gggtcgctga    tctcttcata    aac                                    23

<210> SEQ ID NO 7
<211> LENGTH: 27
<212> TYPE: DNA
<213> ORGANISM: Homo sapiens
<220> FEATURE:

<400> SEQUENCE: 7
gtacagcaga    aagcaagcaa    ctgaatg                                27

<210> SEQ ID NO 8
<211> LENGTH: 28
<212> TYPE: DNA
<213> ORGANISM: Homo sapiens
<220> FEATURE:

<400> SEQUENCE: 8
gaaggaactg    ctttagaatc    caatttcc                               28

<210> SEQ ID NO 9
<211> LENGTH: 31
<212> TYPE: DNA
<213> ORGANISM: Homo sapiens
<220> FEATURE:

<400> SEQUENCE: 9
cacacaggat    ccatggatgc    tgcagatgcg    g                        31

<210> SEQ ID NO 10
<211> LENGTH: 32
<212> TYPE: DNA
<213> ORGANISM: Homo sapiens
<220> FEATURE:

<400> SEQUENCE: 10
cacacaaagc    ttggcttagc    gcctctgccc    tg                       32
```

```
<210> SEQ ID NO 11
<211> LENGTH: 22
<212> TYPE: DNA
<213> ORGANISM: Homo sapiens
<220> FEATURE:

<400> SEQUENCE: 11
cggccgaagg      aacctgaccc      ag                                    22

<210> SEQ ID NO 12
<211> LENGTH: 23
<212> TYPE: DNA
<213> ORGANISM: Homo sapiens
<220> FEATURE:

<400> SEQUENCE: 12
gctggaaccc      tcactaggtt      gcc                                   23

<210> SEQ ID NO 13
<211> LENGTH: 21
<212> TYPE: DNA
<213> ORGANISM: Homo sapiens
<220> FEATURE:

<400> SEQUENCE: 13
ggcccaggct      cggtgaggag      g                                     21

<210> SEQ ID NO 14
<211> LENGTH: 23
<212> TYPE: DNA
<213> ORGANISM: Homo sapiens
<220> FEATURE:

<400> SEQUENCE: 14
ggacgattat      caggagggcc      tgc                                   23

<210> SEQ ID NO 15
<211> LENGTH: 17
<212> TYPE: DNA
<213> ORGANISM: Homo sapiens
<220> FEATURE:

<400> SEQUENCE: 15
gcggcccgag      cagttca                                               17

<210> SEQ ID NO 16
<211> LENGTH: 18
<212> TYPE: DNA
<213> ORGANISM: Homo sapiens
<220> FEATURE:

<400> SEQUENCE: 16
ccatcaggac      catcttca                                              18

<210> SEQ ID NO 17
<211> LENGTH: 23
<212> TYPE: DNA
<213> ORGANISM: Homo sapiens
<220> FEATURE:

<400> SEQUENCE: 17
gctggagcct      gtaacaccgt      ggc                                   23

<210> SEQ ID NO 18
<211> LENGTH: 24
```

-continued

```
<212> TYPE: DNA
<213> ORGANISM: Homo sapiens
<220> FEATURE:

<400> SEQUENCE: 18
gtatatagaa    atactgcaca    gtcc                                    24
```